US00PP12567P2

(12) United States Plant Patent
Kientzler

(10) Patent No.: US PP12,567 P2
(45) Date of Patent: Apr. 23, 2002

(54) NEW GUINEA IMPATIENS PLANT NAMED 'KIMPDEL'

(75) Inventor: Ludwig Kientzler, Gensingen (DE)

(73) Assignee: Paul Erke Ranch, Encinitas, CA (US)

( * ) Notice: Subject to any disclaimer, the term of this patent is extended or adjusted under 35 U.S.C. 154(b) by 0 days.

(21) Appl. No.: 09/639,897

(22) Filed: Aug. 16, 2000

(51) Int. Cl.[7] ..... A01H 5/00
(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of New Guinea Impatiens plant named 'Kimpdel', characterized by its rose pink-colored flowers; freely flowering habit with flowers positioned above or beyond the foliage; upright, spreading, rounded, uniform and compact plant habit; very freely branching growth habit; bushy appearance; dark green and somewhat glossy leaves; and relative resistance to Botrytis.

1 Drawing Sheet

BACKGROUND OF THE INVENTION

The present Invention relates to a new and distinct cultivar of New Guinea Impatiens plant, botanically known as *Impatiens hawkeri*, and hereinafter referred to by the cultivar name Kimpdel.

The new Impatiens is a product of a planned breeding program by the Inventor in Gensingen, Germany. The objective of the breeding program is to develop new Impatiens cultivars with interesting and unique flower and foliage colors.

The new Impatiens originated from a cross made by the Inventor of the *Impatiens hawkeri* selection identified as P 202, not patented, as the male, or pollen parent, with the *Impatiens hawkeri* cultivar Delias, disclosed in U.S. Plant Pat. No. 7,838, as the female, or seed parent. The cultivar Kimpdel was discovered and selected by the Inventor as a flowering plant within the progeny of the stated cross in a controlled environment in Gensingen, Germany in April, 1997.

Asexual reproduction of the new cultivar by terminal cuttings taken at Gensingen, Germany, has shown that the unique features of this new Impatiens are stable and reproduced true to type in successive generations.

SUMMARY OF THE INVENTION

The following traits have been repeatedly observed and are determined to be the unique characteristics of 'Kimpdel'. These characteristics in combination distinguish 'Kimpdel' as a new and distinct Impatiens cultivar:

1. Rose pink-colored flowers.
2. Freely flowering habit with flowers positioned above or beyond the foliage.
3. Upright, spreading, rounded, uniform and compact plant habit.
4. Very freely branching growth habit; bushy appearance.
5. Dark green and somewhat glossy leaves.
6. Relatively resistant to Botrytis.

Compared to plants of the female parent, the cultivar Delias, plants of the new Impatiens are more vigorous, have a more intense flower color, have longer-lasting flowers, and are more resistant to Botrytis. Compared to plants of the male parent, the selection P 202, plants of the new Impatiens are more freely branching and have a lighter flower color.

Plants of the new Impatiens can be compared to plants of the cultivar Dark Delias, disclosed in U.S. Plant Pat. No. 9,139. Plants of the new Impatiens differ from plants of the cultivar Dark Delias in the following characteristics:

1. Plants of the new Impatiens have a more uniform and compact plant habit than plants of the cultivar Dark Delias.
2. Plants of the new Impatiens are more freely branching and are bushier than plants of the cultivar Dark Delias.
3. Plants of the new Impatiens flower about one week earlier than plants of the cultivar Dark Delias.
4. Flower color of the new Impatiens is more intense pink than flower color of the cultivar Dark Delias.
5. Flower of the new Impatiens are larger and flatter than flowers of the cultivar Dark Delias.

Plants of the new Impatiens can be compared to plants of the cultivar Tahiti, disclosed in U.S. Plant Pat. No. 8,601. Plants of the new Impatiens differ from plants of the cultivar Tahiti in the following characteristics:

1. Plants of the new Impatiens have a more uniform plant habit than plants of the cultivar Tahiti.
2. Flower color of the new Impatiens is more intense pink than flower color of the cultivar Tahiti.
3. Flowers of the new Impatiens are longer-lasting than flowers of the cultivar Tahiti.
4. Plants of the new Impatiens are more high temperature tolerant than plants of the cultivar Tahiti.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Impatiens.

The photograph at the top of the sheet comprises a side perspective view of typical flowering plants of 'Kimpdel' grown in a 21.5-cm container.

The photograph at the bottom of the sheet comprises a close-up view of typical developing flower buds, upper surfaces of typical flowers, the lower surface of a typical flower, and the upper and lower surfaces of typical leaves.

DETAILED BOTANICAL DESCRIPTION

The cultivar Kimpdel has not been observed under all possible environmental conditions. The phenotype may vary somewhat with variations in environment such as temperature, light intensity, water status and fertility level, without, however, any variance in genotype. The following observations and measurements describe plants grown in Encinitas, Calif., during the late spring and early summer, under commercial practice in a polyethylene-covered greenhouse with day temperatures about 24° C., night temperatures about 20° C., and light levels generally about 2,750 foot-candles. Plants used in the following description were about 16 weeks old and grown in 21.5-cm containers with three plants per container.

In the following description, color references are made to The Royal Horticultural Society Colour Chart except where general terms of ordinary dictionary significance are used.

Botanical classification: *Impatiens hawkeri* cultivar Kimpdel.

Commercial classification: New Guinea Impatiens cultivar Kimpdel.

Parentage:

*Male parent.*—*Impatiens hawkeri* selection identified as P 202, not patented.

*Female parent.*—*Impatiens hawkeri* cultivar Delias, disclosed in U.S. Plant Pat. No. 7,838.

Propagation:

*Type cutting.*—Terminal cuttings.

*Time to initiate roots.*—Summer: About 15 days at 22° C. Winter: About 20 days at 20° C.

*Time to produce a rooted cutting or liner.*—Summer: About 21 days at 22° C. Winter: About 25 days at 20° C.

*Root description.*—Numerous, fibrous, and freely branching.

Plant description:

*General appearance.*—Upright, spreading, rounded, uniform and compact plant habit. Appropriate for 10 to 25-cm containers; multiple plants are typically planted in larger containers.

*Growth and branching habit.*—Very freely branching with about 10 lateral branches at the base, short internodes, dense and bushy growth. Pinching, that is, removal of the terminal apices, is typically not required. Moderately vigorous to vigorous.

*Crop time.*—From an unrooted cutting, about 16 weeks are required to produce finished flowering plants.

*Plant height.*—About 18 cm.

*Plant diameter.*—About 28 cm.

*Lateral branches.*—Length: About 11 cm. Diameter: About 7 mm. Internode length: About 3.3 cm. Color: 144C blushed (overlaid) with 63A.

*Foliage description.*—Length: About 10 cm. Width: About 4.3 cm. Shape: Elliptic. Apex: Acuminate. Base: Attenuate. Margin: Serrulate with ciliation. Texture: Somewhat glossy. Aspect: Horizontal to somewhat arching. Color: Young foliage, upper surface: 147A. Young foliage, lower surface: 147B. Fully expanded foliage, upper surface: 147A. Fully expanded foliage, lower surface: 147B. Midvein, upper surface: 63D to 63A towards petiole. Midvein, lower surface: 63A. Petiole: Length: About 4.75 cm. Diameter: About 4 mm. Color: 63A.

Flower description:

*Flower type and flowering habit.*—Single rose pink flowers. Freely flowering, usually about 8 flowers and flower buds per lateral branch. Flowers positioned above and beyond the foliage and typically face upward or outward. Flowers mostly flat and squarish to circular in shape. Flowers last about 14 days on the plant depending on temperature and weather conditions. Petals self-cleaning; gynoecium persistent. Not fragrant.

*Flowering season.*—Year-round under greenhouse conditions. In the garden, flowering from spring until fall.

*Flower diameter.*—About 5.25 cm.

*Flower depth.*—About 1.5 cm.

*Flower buds* (*at stage of showing color*).—Rate of opening: From showing color to fully open flower, typically about 2 to 3 days depending on temperature. Length: About 1.3 cm. Diameter: About 6 mm. Shape: Ovoid. Color: 58B.

*Petals.*—Quantity: single, five per flower. Length: Banner petal: About 2.3 cm. Lateral petals: About 2.7 cm. Base petals: About 3 cm. Width: Banner petal: About 4 cm. Lateral petals: About 2.7 cm. Base petals: About 3 cm. Shape: Cordate. Apex: Cordate. Base: Acute. Margin: Entire. Texture: Smooth; velvety. Color: When opening, upper surface: 55A to 55B. When opening, lower surface: 55B. Fully opened, upper surface: 55A to 55B; base, dark pink, 57A. With subsequent development, 55B to 55C. Fully opened, lower surface: 55B to 55C.

*Spur.*—Length: About 4.8 cm. Color: 58A.

*Peduncles.*—Length: About 4.25 cm. Strength: Strong. Angle: Upright to about 45° from vertical. Color: 60D.

*Reproductive organs.*—Androecium: Stamen number: Five fused at anthers, filaments free. Anther shape: Obovate. Total androecium size: About 3 mm by 4 mm. Anther color: 63D. Amount of pollen: Scarce. Pollen color: 155A. Gynoecium: Pistil length: About 4 mm. Stigma color: 155D. Style color: 144C. Ovary color: 144C.

*Seed development.*—Seed development has not been observed.

Disease resistance: Plants of the new Impatiens have been observed to be relatively resistant to Botrytis.

It is claimed:

1. A new and distinct cultivar of New Guinea Impatiens plant named 'Kimpdel', as illustrated and described.

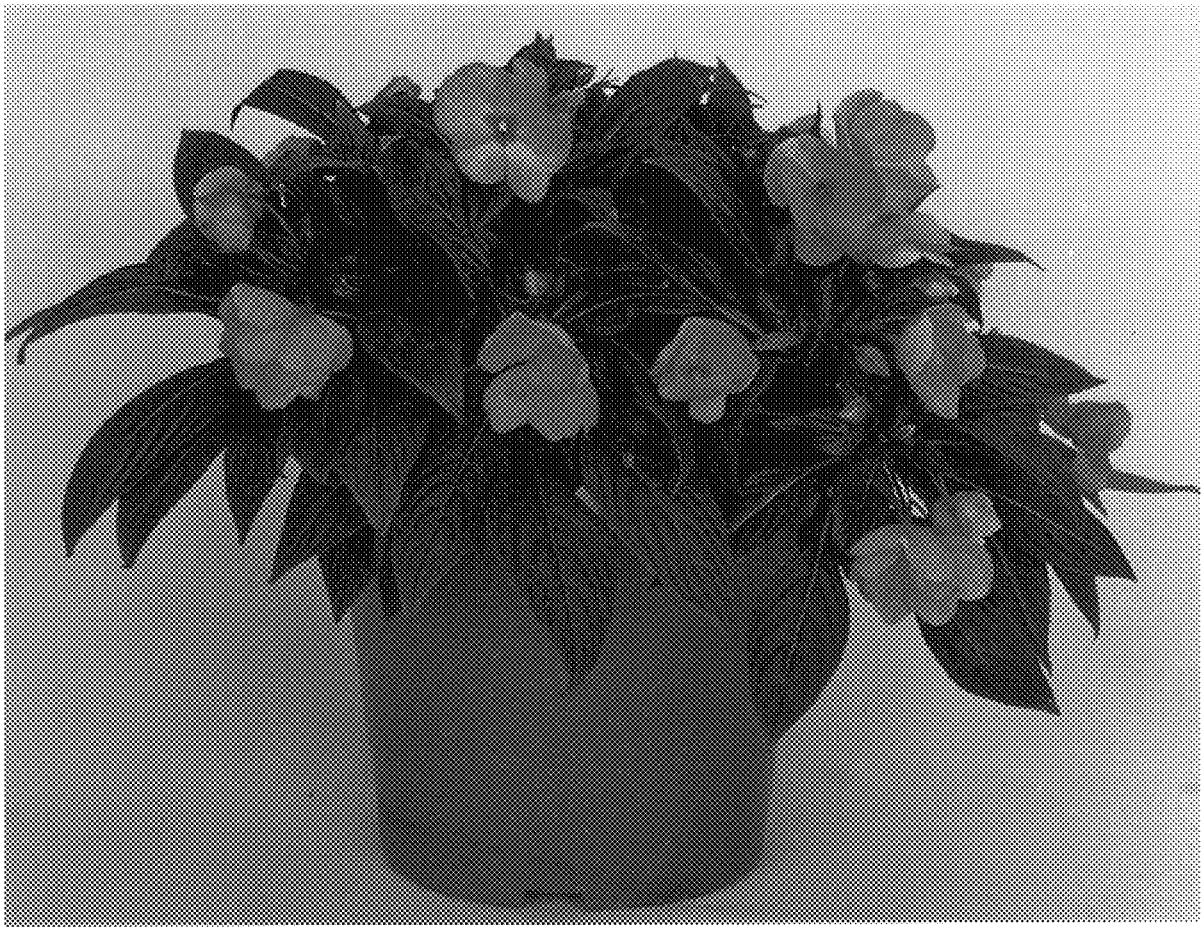
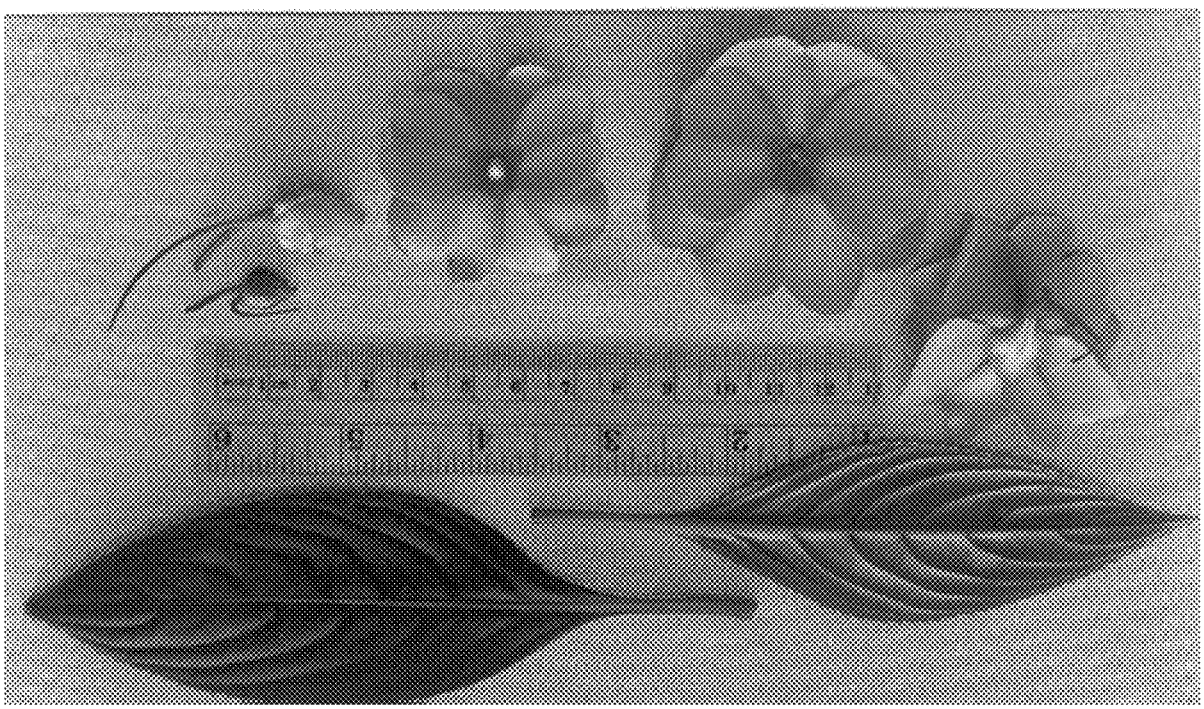

* * * * *